(12) United States Patent
Eutick

(10) Patent No.: US 10,596,102 B2
(45) Date of Patent: Mar. 24, 2020

(54) EMOLLIENT COMPOSITION

(71) Applicant: EUPHARMA PTY LTD., Northbridge (AU)

(72) Inventor: Alec Eutick, New South Wales (AU)

(73) Assignee: EUPHARMA PTY LTD., Northbridge NSW (AU)

( * ) Notice: Subject to any disclaimer, the term of this patent is extended or adjusted under 35 U.S.C. 154(b) by 13 days.

(21) Appl. No.: 15/749,299

(22) PCT Filed: Aug. 4, 2016

(86) PCT No.: PCT/AU2016/050704
§ 371 (c)(1),
(2) Date: Jan. 31, 2018

(87) PCT Pub. No.: WO2017/020087
PCT Pub. Date: Feb. 9, 2017

(65) Prior Publication Data
US 2018/0207086 A1    Jul. 26, 2018

(30) Foreign Application Priority Data

Aug. 4, 2015 (AU) ................................. 2015903098

(51) Int. Cl.
| | | |
|---|---|---|
| *A61K 47/44* | (2017.01) | |
| *A61K 8/92* | (2006.01) | |
| *A61K 8/27* | (2006.01) | |
| *A61Q 19/00* | (2006.01) | |
| *A61K 9/00* | (2006.01) | |
| *A61P 17/16* | (2006.01) | |

(52) U.S. Cl.
CPC ................ *A61K 8/925* (2013.01); *A61K 8/27* (2013.01); *A61K 8/922* (2013.01); *A61K 9/0014* (2013.01); *A61K 47/44* (2013.01); *A61P 17/16* (2018.01); *A61Q 19/007* (2013.01); *A61Q 19/008* (2013.01)

(58) Field of Classification Search
None
See application file for complete search history.

(56) References Cited

U.S. PATENT DOCUMENTS

| | | | | |
|---|---|---|---|---|
| 2002/0012648 A1* | 1/2002 | Orthoefer | .................. | A23J 7/00 424/70.27 |
| 2009/0011042 A1* | 1/2009 | Willimann | ........... | A61K 31/015 424/522 |
| 2009/0068128 A1* | 3/2009 | Waddington | ........... | A61K 8/673 424/59 |
| 2010/0150971 A1* | 6/2010 | Seidling | ................. | A61K 8/046 424/401 |
| 2010/0150989 A1* | 6/2010 | Hoffman | .............. | A61K 9/0024 424/445 |
| 2018/0193244 A1* | 7/2018 | Hood | ........................ | A61K 8/49 |
| 2019/0008747 A1* | 1/2019 | Shibuya | ................. | A61Q 19/08 |

FOREIGN PATENT DOCUMENTS

WO    WO 2010 018418 A1 *    2/2010

OTHER PUBLICATIONS

International Search Report issued in International Application No. PCT/AU2016/050704, dated Oct. 12, 2016.
Written Opinion of the International Searching Authority issued in International Application No. PCT/AU2016/050704, dated Oct. 12, 2016.

* cited by examiner

*Primary Examiner* — Ralph J Gitomer
(74) *Attorney, Agent, or Firm* — Charles C. Achkar; Ostrolenk Faber LLP.

(57) ABSTRACT

The present invention relates to an emollient composition comprising emu oil, jojoba oil, a dermatological base and a metal or metalloid oxide, hydroxide or carbonate. The composition has efficacy in the prevention or treatment of a range of skin conditions.

18 Claims, No Drawings

EMOLLIENT COMPOSITION

CROSS REFERENCE TO RELATED APPLICATIONS

The present application is a § 371 National Phase application based on PCT/AU2016/050704 filed Aug. 4, 2016, which claims priority of Australian Application No. 2015903098, filed Aug. 4, 2015 the subject matter of each of which is incorporated by reference in their entirety.

FIELD OF THE INVENTION

The present invention relates to the field of personal care and skin treatment. More particularly, the invention relates to an emollient composition for the treatment and prevention of skin conditions and symptoms thereof.

BACKGROUND TO THE INVENTION

Any reference to background art herein is not to be construed as an admission that such art constitutes common general knowledge in Australia or elsewhere.

Human skin comprises of two primary layers, the epidermis and the dermis. The epidermis, particularly its outer layer the stratum corneum, serves as a barrier to infection and provides waterproofing, while the dermis is the structural support layer of tissue for the skin located beneath the epidermis and contains nerve endings sensitive to pain, touch and heat, as well as other key structures including veins and arteries and sweat glands.

Many human conditions which require treatment and which may be serious, irritating and potentially painful and dangerous begin at the level of the epidermis and dermis.

Irritating substances that are deposited on the skin may traverse the epidermis and gain access to the underlying tissue which causes inflammation. Inflammation is a non-specific reaction mediated by the immune system in response to a perceived threat or injury and occurs when irritants are able to penetrate the epidermis and initiate secretion of inflammatory mediators. When the layer of skin is compromised as an effective barrier, these irritants will have an unimpeded route into the underlying tissue to cause inflammation, irritation and itchiness.

The layer of skin may be compromised by extended exposure to bodily fluids, bodily wastes, and microorganisms. Bodily fluids and wastes can, themselves, contain irritants in the form of enzymes, such as proteases, ureases and lipases. Alternatively, enzymes can break down proteins and lipids in the skin and release compounds such as free fatty acids, which are also irritants. Bacteria can also convert urine to ammonia resulting in an alkaline environment on the surface of the skin. A common sensation experienced by a person when there is a change in pH and/or the presence of irritants is itchiness. A common reflex to itchiness is to scratch the affected area, which can lead to the exposure of the underlying tissue. If this occurs then the body will be more susceptible to infections and inflammation.

Once the layer of skin has been compromised, the body is also more vulnerable to secondary infections caused by bacteria or fungi. The secondary infection can be by a range of infectious agents, including *Staphylococcus aureus, Staphylococcus epidermis, Propioni bacterium acnes*, and *Pitrosporum ovale*.

Follow on effects from the exposure of the underlying tissue include skin disorders such as rashes (for example, nappy rash and hives), erythema, psoriasis, and bed sores. It is important to alleviate the irritation felt by the body to deter scratching, and therefore deter damage to the skin.

Common therapeutic approaches to prevent and treat skin conditions often rely on the concept of forming a hydrophobic barrier, and using amphoteric oxides. The amphoteric oxides can react with acid or base to act as a buffer to minimize pH changes in the surrounding environment. These amphoteric oxides have astringent properties, which may cause the skin to harden and dry up, and as a result the skin is not able to efficiently absorb any emollient components of the composition. The hydrophobic barrier is intended to physically prevent bodily fluids, bodily wastes and bacteria from being in contact with the skin. The amphoteric oxides, and hydrophobic barrier, together are designed to alleviate the problems associated with irritation, itchiness and scratching.

Other conditions affecting the skin can include burns, particularly sunburn or ultra violet light damage. Here the epidermis, and often the dermis, is damaged and there is a need for both an occlusive barrier to prevent ingress of harmful micro-organisms as well as the egress of moisture. A typical sufferer will also have inflammatory swelling and intense pain and itching which require treatment. Similarly, analogous conditions such as cuts and bruising, painful stings from plants, ants and sea creatures etc. and other damaging injury may need to be treated in the same manner.

There are many currently utilized therapeutic compositions containing natural and/or petrochemical products as well as a wide array of synthetic and semi synthetic excipients such as polyethylene glycols, polyacrylamides, copolymers of ethylene oxide and propylene oxide or poly-ethoxylated castor oils and the like. Many of these compositions are high in oil content and often greasy to the touch. Sufferers may report allergic reactions to some of the semi and fully synthetic excipients and/or the non natural preservatives utilised in these compositions, such as parabens and phenoxyethanol. These compositions are highly mobile and will spread from where they are applied to the surrounding unaffected areas, resulting in less composition remaining on the affected areas. In the case of nappy rash, for example, they potentially also transfer damaging faeces, urine and other irritants to these previously unaffected skin areas. These high oil compositions can also remain on the surface of the skin for an extended period of time and can be transferred easily to garments and clothes which is undesirable both due to the damage to the clothing and because of the removal of the barrier effect. In other instances, hydrogels made from polyurethanes, polyesters, or nylon polymer mixtures are utilised and they similarly have a problem with spreading.

There is a need for new approaches to solve one or more of the problems recited above.

SUMMARY OF THE INVENTION

The present invention is directed to emollient compositions that are useful for treating and/or preventing skin conditions and/or symptoms thereof. It is predicated, at least in part on the finding that an emollient composition comprising emu oil, jojoba oil, a metal or metalloid oxide, hydroxide or carbonate and a dermatological base can be applied to damaged areas of the skin to prevent harmful substance and microorganisms penetrating those areas and to prevent further damage being incurred from contact with bodily wastes such as faeces from nappies, pus from bed sore, old blood and the like. The compositions are also suitable for purely preventative use on undamaged skin or skin which is at risk of developing damage.

Without wishing to be bound by any particular theory, it has been found that the use of lanolin and white paraffin create a matrix barrier which prevents the ingress of harmful substances and prevents the egress of moisture while also holding the metal or metalloid oxide, hydroxide or carbonate close to the skin along with the efficacious emu oil and jojoba oil which are allowed to pass through the matrix and penetrate the outer dermis to maintain suppleness of the skin while reducing infection, irritation, inflammation, swelling, itching and the like. The metal or metalloid oxide, hydroxide or carbonate provides pH buffering while imparting desirable physical characteristics to the composition. The composition has a number of advantageous physical properties in that it does not present with a greasy or oily feel; it stays on the skin and does not rub off onto clothing easily; it has a good degree of workability in the hands; and it can be formulated at room temperature i.e. heating during the blending process is not required.

In a broad aspect, the invention resides in an emollient composition comprising emu oil, jojoba oil and a dermatological base.

In a first aspect, the invention resides in composition comprising in % by weight amounts of the composition:
  (a) about 2.5% to about 15% emu oil;
  (b) about 4% to about 25% jojoba oil;
  (c) about 25% to about 75% of a dermatological base; and
  (d) about 10% to about 40% of a metal or metalloid oxide, hydroxide or carbonate.

In a second aspect, the invention resides in a method of treating and/or preventing a skin condition in a subject, the method including the step of administering to the skin of the subject a therapeutically effective amount of an emollient composition comprising, in % by weight amounts of the composition:
  (a) about 2.5% to about 15% emu oil;
  (b) about 4% to about 25% jojoba oil;
  (c) about 25% to about 75% of a dermatological base; and
  (d) about 10% to about 40% of a metal or metalloid oxide, hydroxide or carbonate.

In a third aspect, the invention resides in a method of formulating an emollient composition including the step of combining and mixing emu oil, jojoba oil, a dermatological base and a metal or metalloid oxide, hydroxide or carbonate to form the emollient composition in the following % by weight amounts of the composition:
  (a) about 2.5% to about 15% emu oil;
  (b) about 4% to about 25% jojoba oil;
  (c) about 25% to about 75% dermatological base; and
  (d) about 10% to about 40% metal or metalloid oxide, hydroxide or carbonate.

In a fourth aspect, the invention resides in the use of an emollient composition comprising, in % by weight amounts of the composition:
  (a) about 2.5% to about 15% emu oil;
  (b) about 4% to about 25% jojoba oil;
  (c) about 25% to about 75% of a dermatological base; and
  (d) about 10% to about 40% of a metal or metalloid oxide, hydroxide or carbonate,
in the preparation of a medicament for use in the treatment and/or prevention of a skin condition in a subject.

The medicament is as described herein for the emollient composition of the first aspect.

The emollient composition is therefore a cream for topical administration.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION OF THE INVENTION

In this specification, adjectives such as additional, and the like may be used solely to distinguish one element or action from another element or action without necessarily requiring or implying any actual such relationship or order. Words such as "comprises" or "includes" are intended to define a non-exclusive inclusion, such that a composition or method that comprises a list of elements does not include only those elements but may include other elements not expressly listed, including elements that are inherent to such a composition or method.

The terms "treat", "treatment" or treating", as used herein, refer to a therapeutic intervention that ameliorates a sign or symptom of a skin condition after it has begun to develop. The term "ameliorating," with reference to skin conditions, refers to any observable beneficial effect of the treatment. The beneficial effect can be determined using any methods or standards known to the ordinarily skilled artisan.

By "prevent", "preventing" or "preventative" is meant prophylactically administering the composition to a mammal who does not exhibit signs or symptoms of a skin condition, but who is expected or anticipated to likely exhibit such signs or symptoms in the absence of prevention. Preventative treatment may at least lessen or partly ameliorate expected symptoms or signs.

As used herein, "skin condition" refers to a dermatological disease, which includes but is not limited to states of distress of the skin, rashes, burns, cuts, abrasions, inflammation, dry skin, pruritis, rubor, dermatitis, eczema, urticarial and erythema.

The terms "effective amount" or "therapeutically effective amount" describes a quantity of the composition of the first aspect sufficient to achieve a desired coverage and consequent outcome in a subject being treated. In some embodiments, a "therapeutically effective amount" is sufficient to treat and/or prevent skin conditions. The "therapeutically effective amount" may vary, in a manner which would be understood by a person of skill in the art, with the patient's age, sex, weight, severity of the skin condition etc.

As used herein, "inflammation" refers to the well-known localised response to various types of conditions or infections, which is characterised by redness, heat, swelling, itchiness and pain. Inflammation represents an early defense mechanism to contain an infection and prevent its spread from the initial focus and to deliver repair messages. Major events in inflammation include dilation of capillaries to increase blood flow, changes in the microvasculature structure, leading to escape of plasma, proteins, and leukocytes from circulation, and leukocyte emigration from the capillaries and accumulation at the site of the condition or infection.

The term "about" as used herein in relation to the amount of a component, means that the amount is nominally the number following the term "about" but the actual amount may vary from this precise amount to an unimportant degree.

Unless defined otherwise, all technical and scientific terms used herein have the same meaning as would be commonly understood by those of ordinary skill in the art to which this invention belongs.

In one broad aspect, the invention resides in an emollient composition comprising emu oil, jojoba oil and a dermatological base.

In a first aspect, the invention resides in an emollient composition comprising in % by weight amounts of the composition:
(a) about 2.5% to about 15% emu oil;
(b) about 4% to about 25% jojoba oil;
(c) about 25% to about 75% of a dermatological base; and
(d) about 10% to about 40% of a metal or metalloid oxide, hydroxide or carbonate.

The emollient composition is useful for treating and/or preventing a skin condition.

Preferably, the composition is a topical composition.

Suitably, the composition is a substantially homogenous cream or lotion.

The % by weight amount of the emu oil in the composition is suitably from about 0.1% to about 50%, preferably from about 1% to about 35%, more preferably from about 2.5% to about 15%, even more preferably about 3% to about 12%, and still more preferably from about 4% to about 10%, including about 5%, 6%, 7%, 8% and 9%. A preferred range is greater than 5% to less than about 9% by weight of the composition such as 5.5% to 9%.

The term "emu oil" as used herein may refer to any oil that is derived from adipose tissue harvested from emus. Emu oil may also be derived from any of the subspecies, *Dromaius novaehollandiae*. Without being bound to any particular constituent, reference herein to emu oil may be considered to include one or more chemical compounds selected from oleic acid, omega-6 fatty acids, stearic acid, palmitic acid, linoleic acid, and/or linolenic acid. These chemical compounds can be produced synthetically or derived from another source including essential oils and used in the present composition. It is preferred, however, that the oil is harvested from an Emu species.

The % by weight amount of jojoba oil in the composition is suitably from about 0.1% to about 50%, preferably from about 1% to about 35%, more preferably from about 4% to about 25%, even more preferably about 6% to about 20%, and still more preferably from about 8% to about 18%, including about 9%, 10%, 11%, 12%, 13%, 14%, 15%, 16% and 17%. A preferred range is greater than 10% to less than about 15% by weight of the composition.

The term "jojoba oil" as used herein refers to any oil that is derived from the seed of the Jojoba plant including purified and/or refined derivatives of jojoba oil. The jojoba oil can be extracted by employing a number of methods known to a person skilled in the art, such as steam distillation, or mechanical or chemical means. Without being bound to any particular constituent, reference herein to jojoba oil may be considered to include one or more chemical compounds selected from docosdienoic acid, 11-eiconsenoic acid, 9-godoelic acid, docosenoic acid, oleic acid, and/or palmitoleic acid. These chemical compounds can alternatively be produced synthetically or derived from another source including essential oils and used in the present composition.

Typical compositions for treating skin conditions are greasy and not sufficiently viscous, and require the patient to rub or work the composition onto and around the affected area and into the skin. The addition of jojoba oil and emu oil provide the present composition with superior penetrability and therefore effective absorbance of other components whilst providing a range of advantageous properties in and of themselves. The composition is also highly malleable which makes it easy to apply precisely to the affected area where it is quickly absorbed before it can be rubbed off onto clothes or garments.

Prior art compositions often use methylsulfonylmethane or urea to penetrate the skin which can have harmful side effects. The present composition achieves its purpose without the use of harmful components. It is one advantage of the present invention that no further diluents or excipients are required other than the components mentioned above. However, depending of the mode of administration or formulation and manufacture considerations it may, at times, be useful to include one or more carriers, excipients, diluents and the like as are known in the art.

The astringent properties of zinc oxide in prior art compositions cause mild coagulation of the skin proteins, which hardens and dries the skin. As such, the skin could be less receptive to absorbing the composition. The addition of the jojoba oil with an amphoteric oxide, and/or other metal oxide, and dermatological base alleviates this problem through its emollient properties which help to counteract the astringent effects of the amphoteric oxide. As such, the absorption properties of the composition allow the composition to penetrate deeper and be absorbed into the skin even in the presence of the astringent amphoteric oxides.

The properties contributed by the jojoba oil include increased workability during formulation of the composition. This is a distinct advantage of the present composition as without the jojoba the dermatological base of emollients and the amphoteric oxides or other metal oxides may form a viscous mass which is extremely difficult to manipulate and which requires extensive cleaning of the machinery following mixing.

The emu oil, while also assisting in improving the workability of the composition, also provides antibacterial and anti-inflammatory properties thereto and so inherently protects the skin from possible bacterial and fungal infection while the anti-inflammatory components counter skin irritation and inflammation. Its ability to penetrate the epidermal lipid barrier acts to lessen the risk of skin dehydration by continuously hydrating the skin, providing a moist environment and providing skin nutrients aiding protection and repair of damaged tissue.

In summary, the emu oil provides significant benefits to the present composition through: (i) its ability to act as a dermal penetrant and medicament carrier; (ii) its anti-inflammatory properties; (iii) its ability to act as an emollient/moisturizer, (iv) its bacteriostatic properties; (v) its low potential for irritation of the skin; and (vi) its non-comedogenic properties (it does not clog up the pores).

The % by weight amount of the dermatological base in the composition is suitably from about 10% to about 80%, preferably from about 25% to about 75%, more preferably from about 30% to about 70%, even more preferably from about 35% to about 67%, and most preferably from about 40% to about 65%. A preferred range is greater than 45% to less than about 60% by weight of the composition such as 48% to 55%.

The dermatological base comprises at least one emollient.

The term "emollient" as used herein in relation to the composition, can be interchanged with moisturizer, and includes occlusive emollients, humectants emollients, anti-pruritic emollients and antiseptic emollients.

In certain embodiments, the at least one emollient is a petrochemical emollient and/or a natural emollient.

Typically, petrochemical emollients are derived using energy intensive methods, such as high temperature production methods. The petrochemical emollient can be oleochemical products derived from vegetable oil, or substances derived from petrochemical materials.

In one embodiment, the petrochemical emollient is selected from the group consisting of mineral oils, petroleum jelly, fatty acids, triglycerides, glycols (including ethylene glycols such as PEG), glycerol stearate, hydrogenated oils, paraffin, stearic acid, castor oil, ethoxylated and ethoxylated hydrogenated castor oils and petrochemical based substances. A person skilled in the art will recognize that the list provided is not exhaustive and will understand that there are further known suitable petrochemical emollients. These petrochemical emollients may be produced synthetically, or derived from a natural source.

In one embodiment, the petrochemical emollient is white soft paraffin.

The % by weight amount of the petrochemical emollient, such as white soft paraffin, in the composition is suitably from about 10% to about 50%, more suitably about 15% to about 40%, and preferably from about 20% to about 30%, including about 22% to about 28%.

Natural emollients are emollients that are not typically produced using energy intensive conditions, such as high temperatures. High temperatures can cause nutrients, antioxidants and some fatty acids to decompose.

In one embodiment, the natural emollient is an oil, fat or wax which is derived from a natural source, such as plants, fruits, seeds, insects, or animals. In certain embodiments, the natural emollient is selected from the group consisting of lanolin, shea butter, cocoa butter, mineral oil, beeswax, carnauba or palm wax, squalene, coconut oil, almond oil, olive oils and sesame oils. It is preferred that the natural emollient is an extract comprised largely of long chain waxy esters. It will be appreciated by a person skilled in the art that this list of natural emollients is not an exhaustive list, and is representative only. These natural emollients can themselves be made up of a number of chemicals and these chemicals can be produced synthetically or derived from another source.

In one embodiment, the natural emollient is lanolin or a lanolin-based emollient.

The % by weight amount of the natural emollient, such as lanolin, in the composition is suitably from about 10% to about 50%, more suitably about 15% to about 40%, and preferably from about 20% to about 30%, including about 22% to about 28%.

In certain embodiments, the dermatological base comprises at least two emollients wherein one is a petrochemical emollient and one is a natural emollient.

In these embodiments it is preferred that the petrochemical emollient is white soft paraffin and that the natural emollient is selected from shea butter, beeswax, lanolin or a lanolin-based emollient. Preferably, the natural emollient is lanolin or a lanolin-based emollient.

In one embodiment, the composition further comprises a preservative. The preservative may not be necessary if the composition is to be used shortly after manufacture but is preferred for storage.

The preservative is a substance that is added to the composition to prevent microbial growth and undesirable chemical changes. The preservative can be naturally derived, or a synthetically produced. The preservative may be selected from the group consisting of antioxidants, anti-microbial additives, benzylalcohol, caprylic acid, carrylyl glycol, EDTA, phenoxyethanol, tocopherol, BHT, potassium sorbate, tea tree oil, parabens, anti-fungals and *Eucalyptus* oil. It will be appreciated by a person skilled in the art that this is not an exhaustive list of suitable preservatives but serves to illustrate some of the possible options.

In one embodiment, the preservative is a plant-derived oil including those derived from the wood, stem, bark, flowers or leaves of a plant, shrub or tree. The use of an oil as the preservative may provide advantages to the physical properties and feel on the skin of the composition.

In preferred embodiments, the preservative is *Eucalyptus* oil.

The term "*Eucalyptus* oil" as used herein refers to any oil that is derived from *Eucalyptus* leaves including purified and/or refined derivatives of *Eucalyptus* oil. *Eucalyptus* oil may be derived from the leaves of *Eucalyptus* and any of its cultivars or from another species of Myrtaceae. The *Eucalyptus* oil can be extracted in a number of methods known to a person skilled in the art, such as steam distillation, mechanical or chemical means. Without being bound to any particular constituents, *Eucalyptus* oil may include cineole. This chemical compound may be produced synthetically or may be derived from other sources.

Preferably, the *Eucalyptus* oil contains at least 70% by weight of cineole.

The % by weight amount of the preservative in the composition is suitably from about 0.1% to about 20%, more suitably about 0.5% to about 10%, and preferably from about 1.0% to about 6%, including about 2%, 3%, 4% and 5%. A preferred range is greater than 2% to less than about 5% by weight of the composition such as 2.5% to 4.5%.

In one embodiment, the composition may, in addition to *Eucalyptus* oil, further comprise a piroctone salt or derivative as an anti-fungal agent. A preferred salt is piroctone olamine, the ethanolamine salt of piroctone.

The piroctone salt or derivative may be present in the composition in an amount from about 0.01% to about 2% by weight, about 0.05% to about 1.5%, or about 0.1% to about 1.0% inclusive of about 0.15%, 0.20%, 0.25%, 0.3% and 0.35% by weight.

In certain embodiments, the composition further comprises a metal or metalloid oxide, hydroxide or carbonate.

The % by weight amount of the metal or metalloid oxide, hydroxide or carbonate in the composition is suitably from about 5% to about 50%, preferably from about 10% to about 40%, more preferably from about 15% to about 35%, and most preferably from about 20% to about 30% including values of about 21%, 22%, 23%, 24%, 25%, 26%, 27%, 28% and 29%. A preferred range is greater than about 22% to less than about 28% by weight of the composition such as 23% to 27%.

The metal or metalloid may be selected from the group consisting of aluminium, zinc, lead, iron, barium, tin, titanium, silicon, beryllium, magnesium and calcium. Each of these metals or metalloid may be combined, as appropriate, to form an oxide, hydroxide or carbonate.

In embodiments, the metal or metalloid oxide, hydroxide or carbonate may be selected from the group consisting of aluminium oxide, tin oxide, zinc oxide, lead oxide, beryllium oxide, iron oxide, magnesium oxide, calcium oxide, titanium dioxide, silicon dioxide, aluminium hydroxide, zinc hydroxide, magnesium carbonate, calcium carbonate, aluminium carbonate, zinc carbonate, iron carbonate, and barium carbonate.

The metal or metalloid oxide, hydroxide or carbonate may be one or more transition metal oxides, hydroxides or carbonates.

In certain preferred embodiments, the metal or metalloid oxide, hydroxide or carbonate comprises an amphoteric oxide. The amphoteric oxide may be selected from the group consisting of zinc oxide, aluminium oxide, titanium dioxide, or iron (III) oxide.

The metal or metalloid oxide, hydroxide or carbonate, preferably an amphoteric oxide with optional further insoluble metal oxide, may be present in the composition to alleviate problems associated with pH change. An amphoteric oxide, and/or other metal oxide, such as iron oxide, is capable of reacting as an acid or a base to act as a buffer to minimize pH changes in the surrounding environment, and therefore alleviates the irritation experienced when there is a pH change at the surface of the skin. Such a pH change may be caused by microbial activity which can bring about a pH driven burning, itching or other irritation sensation in the subject.

It has also unexpectedly and advantageously been found that the metal or metalloid oxide, hydroxide or carbonate, such as an amphoteric oxide, contributes to providing an optimal viscosity, application feel and workability to the composition compared with the composition when it is absent. This reduces the need for higher amounts or, for example, lanolin or other viscosing agents thereby unexpectedly providing dual benefits in the composition. It has not previously been realised that metal or metalloid oxide, hydroxide or carbonate could, in relatively high amounts by weight of an emollient composition, positively affect the physical feel and workability characteristics thereof.

Preferably, the amphoteric oxide is zinc oxide.

In one embodiment, the metal or metalloid oxide, hydroxide or carbonate is present, at least in part, in the form of calamine. Calamine is formed from zinc oxide as an amphoteric oxide and iron oxide as an insoluble metal oxide, with some blends comprising zinc carbonate.

The calamine preferably comprises zinc oxide and iron (III) oxide. The % by weight amount of zinc oxide in the calamine is suitably from about 95% to about 99.9%, more suitably about 98% to about 99.9%, and more preferably about 99% to about 99.9%, and most preferably about 99.5%. The % by weight amount of iron (III) oxide in the calamine is suitably from about 0.1% to about 5%, more suitably about 0.1% to about 2%, more preferably about 0.1% to about 1%, and most preferably about 0.5%.

The metal or metalloid oxide, hydroxide or carbonate may be present in the composition as calamine and a further amount of a metal or metalloid oxide, hydroxide or carbonate, for example, zinc oxide. In certain embodiments, the composition comprises calamine at from about 5% to about 20% by weight of the composition, preferably from about 8% to about 15% and, additionally, an amount of metal or metalloid oxide, hydroxide or carbonate in the same % by weight of the composition ranges. Therefore, in one embodiment, the composition comprises from about 5% to about 20% calamine and from about 5% to about 20% metal or metalloid oxide, hydroxide or carbonate, preferably from about 8% to about 15% calamine and from about 8% to about 15% metal or metalloid oxide, hydroxide or carbonate, more preferably from about 10% to about 14% calamine and from about 10% to about 14% metal or metalloid oxide, hydroxide or carbonate. The metal or metalloid oxide, hydroxide or carbonate may be selected from those previously recited but a preferred example is zinc oxide.

In one embodiment, the composition of the first aspect comprises, in % by weight amounts of the entire composition, about 10% to about 15% jojoba oil, about 5% to about 10% emu oil, about 2% to about 5% *Eucalyptus* oil, about 20% to about 30% metal or metalloid oxide, hydroxide or carbonate, which amount may optionally include calamine and a separate metal or metalloid oxide, and about 40% to about 60% dermatological base.

In one embodiment, the composition of the first aspect comprises, in % by weight amounts of the entire composition, about 10% to about 15% jojoba oil, about 5% to about 10% emu oil, about 2% to about 5% *Eucalyptus* oil, about 10% to about 15% zinc oxide, about 10% to about 15% calamine, about 15% to about 35% of a petrochemical emollient, such as white soft paraffin, and about 15% to about 35% of a natural emollient selected from the group consisting of lanolin, shea butter, cocoa butter, mineral oil, beeswax, carnauba or palm wax, squalene, coconut oil, almond oil, olive oils and sesame oils.

Preferably, the petrochemical emollient is white soft paraffin and the natural emollient is lanolin.

In one embodiment, the composition of the first aspect consists of, or alternatively consists essentially of, jojoba oil, emu oil, *Eucalyptus* oil, calamine, zinc oxide, lanolin and white soft paraffin oil. The relative amounts of each component may be selected individually from any of those as previously described.

In one specific embodiment, the emollient composition further comprises an antioxidant and diuretic such as caffeine.

In a further embodiment, the emollient composition further comprises an agent selected from the group consisting of a polyphenol antioxidant, a procyanidin, a sulphonated polysaccharide and a flavenoid. When the component is a polyphenol antioxidant it may be epigallocatechin gallate.

It has been found that the addition of relatively small amounts of caffeine, or caffeine sodium benzoate into a topical application can decrease the number of malignant and nonmalignant tumors which may present on a mammals skin. It will be appreciated by a person skilled in the art that the caffeine, or caffeine sodium benzoate can be obtained from natural sources or produced synthetically.

A further benefit may be obtained when epigallocatechin gallate is present with caffeine in the topically applied emollient composition in that it has been found in the art that there is a further decrease in the presentation of malignant and nonmalignant tumors when compared to subjects not treated with the composition. Again, it will be appreciated by a person skilled in the art that the epigallocatechin gallate can be obtained from natural sources or produced synthetically. The polyphenol antioxidant, procyanidin, sulphonated polysaccharide and flavenoid components may provide for the same benefits.

In one embodiment, the composition may further comprise an extract or preparation from a plant of the genus *Arnica*. This extract or preparation may assist with encouraging the healing of bruising on the skin.

The emollient composition of the first aspect has a desirable viscosity profile, emollient and water-repellent properties, and can maintain a barrier between an irritant and the skin. The desirable viscosity profile allows the composition to be isolated over a small surface area to provide the affected area with a greater amount of composition to treat and/or prevent a skin condition. The composition also forms a barrier over the skin that will prevent bodily fluid, bodily wastes, irritants and bacteria from being in contact with the skin. This barrier will alleviate possible irritation experienced by the patient and will also help to prevent the layer of skin from being compromised.

Although the present composition has a relatively high oil content, it does not have a correspondingly greasy feel on the skin due to a reduced amount of composition remaining on the surface of the skin because of the penetrant properties of jojoba oil and emu oil. The emollient properties of the composition allow for efficient and faster penetration into the skin, and as such the composition resides on the surface of the skin for a reduced time period. The smaller amount of composition on the surface of the skin will still form a barrier between any irritants and the skin, and minimizes the amount of composition that can be rubbed off onto garments or clothing. Hence, the absorption properties alleviate the problems associated with the composition rubbing off onto garments and/or clothing. The dermatological base, particularly the lanolin when present, assists in preventing moisture loss from the skin and so effectively locks in moisture.

Further, it is a distinct advantage of the present composition that it can be formulated from start to finish at room temperature or thereabouts. Many prior art emollient compositions require temperatures above 40° C., 50° C., or higher to achieve a reasonable blend of the various ingredients. The present composition uses emu oil in significant quantities and temperatures above 40° C. can destroy many of the beneficial components of that oil so the ability to blend at room temperature provides for a more efficacious final product. Therefore, in one embodiment, the composition of the first aspect is prepared or blended at a temperature of less than 40° C., preferably less than about 35° C., more preferably less than about 30° C. or 25° C.

In one embodiment, the pH of the emollient composition will be within the range of 4.5 to 8.0, preferably 5.0 to 7.5 and more preferably about 5.5 to 6.5. The pH of the composition may be important in ensuring further irritation is not caused when applied to damaged skin.

In a second aspect, the invention resides in a method of treating and/or preventing a skin condition in a subject, the method including the step of administering to the skin of the subject a therapeutically effective amount of an emollient composition comprising, in % by weight amounts of the composition:
(a) about 2.5% to about 15% emu oil;
(b) about 4% to about 25% jojoba oil;
(c) about 25% to about 75% of a dermatological base; and
(d) about 10% to about 40% of a metal or metalloid oxide, hydroxide or carbonate.

The composition may be as described in any one or more embodiments of the first aspect.

Preferably, the step of administering the composition is a step of topical administration.

In one embodiment, the skin condition may be selected from the group consisting of dry skin, nappy rash, erythema, psoriasis rashes, bed sores, allergic rashes, acne, rosacea, minor skin infections, and other skin irritation rashes.

The amount of the composition prescribed to a subject may vary depending on the manner of administration, nature and severity of the symptoms, age and body weight of the subject. Under certain circumstances, however, higher or lower daily amounts of the composition may be appropriate. The administration of the composition can be carried out both by single administration in the form of an individual application or else several smaller applications and also by multiple applications at specific intervals. As the composition does not contain any toxic agents it may be that the patient can simply apply the composition as needed in the affected areas.

Preferred embodiments of the composition are in the form of a topical solution, lotion, shake solution, cream, ointment, gel, sprayable lotion, sprayable solution, sprayable foam, foam or balm.

In a third aspect, the invention resides in a method of formulating an emollient composition including the step of combining and mixing emu oil, jojoba oil, a dermatological base and a metal or metalloid oxide, hydroxide or carbonate to form the emollient composition in the following % by weight amounts of the composition:
(a) about 2.5% to about 15% emu oil;
(b) about 4% to about 25% jojoba oil;
(c) about 25% to about 75% dermatological base; and
(d) about 10% to about 40% metal or metalloid oxide, hydroxide or carbonate.

In a fourth aspect, the invention resides in the use of an emollient composition comprising, in % by weight amounts of the composition:
(a) about 2.5% to about 15% emu oil;
(b) about 4% to about 25% jojoba oil;
(c) about 25% to about 75% of a dermatological base; and
(d) about 10% to about 40% of a metal or metalloid oxide, hydroxide or carbonate,
in the preparation of a medicament for use in the treatment and/or prevention of a skin condition in a subject.

The emollient composition of the third and fourth aspects is as described herein for any one or more embodiments of the emollient composition of the first aspect. The skin condition may be as previously described for the second aspect.

In one embodiment, the method of formulating the composition of the first aspect further includes adding and mixing a preservative.

A vessel used for the mixing operation is a chemical resistant vessel which does not react with the composition and has a variable speed stirring.

The constituents can be added in any order and stirred for a predetermined amount of time before the addition of each constituent.

Preferably, the emu oil and jojoba oil are added to a metal or metalloid oxide, hydroxide or carbonate, preferably an amphoteric oxide with a further optional metal oxide, such as an iron oxide, and subsequently the dermatological base is added.

Preferably, the combining and mixing are carried out at below 40° C.

EXAMPLES

Example 1—Sample Composition

An emollient composition according to one embodiment of the invention for treating and/or preventing inflammation, and other conditions as described herein, was prepared containing the relative amounts of ingredients shown in Table 1 below. The composition was prepared by the process described in Example 2.

TABLE 1

Sample Composition

| Component | Amount (Kg) |
| --- | --- |
| Emu Oil | 7 |
| *Eucalyptus* Oil | 3.4 |
| Jojoba Oil | 12.6 |
| Lanolin | 26 |
| White soft paraffin | 26 |
| Calamine | 12.5 |
| Zinc Oxide | 12.5 |
| Total | 100 |

Example 2—Example Manufacturing Process

The following working steps were taken to produce a composition for treating and/or preventing inflammation with the relative amounts as set out in table 1:
- a. add finely sieved calamine and zinc oxide together into a suitably sized vessel and mix;
- b. weigh out and add jojoba oil to the above powders while mixing;
- c. weigh out and add emu oil to the above powders while mixing;
- d. weigh out and add *Eucalyptus* oil to the above powders while mixing;
- e. stirring for about 10 minutes until all of the above ingredients are evenly dispersed;
- f. weigh out lanolin and white soft paraffin and add these to a separate vessel whilst stirring to combine the two to achieve a smooth consistency and then add to the above powder and oils mixture;
- g. mixing the resultant composition until homogenous with a smooth consistency or alternatively putting the mixture through a milling process but, either way, ensuring all ingredients are evenly dispersed with no lumps or chunks of dry powder remaining; and
- h. filling suitably sized containers with the composition.

The mixing/stirring steps in this process may be performed at room temperature and no heating is required which is a significant advantage flowing from the physical properties provided to the composition by the key components.

Example 3—Further Sample Composition

An emollient composition according to one further embodiment of the invention for treating and/or preventing inflammation, and other conditions as described herein, was prepared containing the relative amounts of ingredients shown in Table 2 below. The composition was prepared largely by the process described in Example 2 with the further addition of piroctone olamine which can be added as the final component into the mixture following step f of example 2.

TABLE 2

Further Sample Composition

| Component | Amount (g) |
| --- | --- |
| Emu Oil | 7 |
| *Eucalyptus* Oil | 3.4 |
| Jojoba Oil | 12.6 |
| Lanolin (ultra-pure) | 25.9 |
| White soft paraffin (Vaseline) | 25.9 |
| Calamine | 12.5 |
| Zinc Oxide | 12.5 |
| Piroctone olamine | 0.2 |
| Total | 100 |

Example 4—Further Sample Composition

A composition of just the components of the dermatological base along with two metal oxides i.e. a mixture of (i) calamine; (ii) zinc oxide; (iii) lanolin; and (iv) white soft paraffin, resulted in a composition that was oily, inconsistent, and had solid aggregates. The addition of the emu oil and the jojoba oil to the dermatological base plus oxides therefore surprisingly resulted in a composition that was smooth, less greasy with a consistent viscosity profile and no observable aggregates. The addition of the emu oil and jojoba oil therefore resulted in a composition that is easier to manufacture, whilst improving the penetration of the composition, and giving a more desirable viscosity profile.

Example 5—Application in the Treatment of Rashes

A composition of the first aspect was prepared to have the composition described in table 1. Two people were treated for severe rashes/dermatitis with the composition. The dose was approximately 0.2 mL (equivalent to 0.2 gm) of the composition applied to about 45 sq cm of affected skin two or three times a day. Both people remarked on how easy and painless it was to spread the composition on sore rashes. Both people reported ease of spreading and fast absorption into the skin so there was no transfer onto clothes.

Patient one was a male 55 years old with no other clinical conditions other than a severe rash on the inner side of his upper arm and a second very severe and possibly infected rash under his arm. Both rashes reported as very itchy and painful with raised red welts and pimples. He had previously applied hydrocortisone gel which, he reported, made the condition of the rashes worse, including stripping the skin. He had tried to use Bepanthen® but found it far too hard and painful to spread and felt it did not work. He reported it felt too "sticky".

The patient applied the composition to the affected regions 2-3 times daily for 4 days. He reported an almost immediate effect on itch and complete control and absence of the rash at about 4 days. The composition was non-irritating, easy to apply and quickly absorbed.

Patient two was a female of about 50 years of age presenting with no clinical conditions other than two rash episodes described as follows: (i) flat and red and sore/itchy rash on hand, described as a dermatitis. This condition was reported as having cleared with 1-2 days use with coverage over the rash area and application twice a day; (ii) raised and red, painful, itchy and sore rash on bottom from rowing i.e. likely a friction rash. The composition of table 1 was applied twice a day and the rash in this instance resolved completely in 2-3 days.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. An emollient composition comprising in % by weight amounts of the composition:
   - (a) about 2.5% to about 15% emu oil;
   - (b) about 4% to about 25% jojoba oil;
   - (c) about 25% to about 75% of a dermatological base wherein the dermatological base comprises at least two emollients wherein one is a petrochemical emollient and one is a natural emollient and wherein the petrochemical emollient is selected from petroleum jelly and paraffin and the natural emollient is selected from shea butter, beeswax, lanolin and a lanolin-based emollient; and (d) about 10% to about 40% of a metal or metalloid oxide, hydroxide or carbonate.

2. The composition of claim 1 wherein the dermatological base comprises, in % by weight of the composition, between about 20% to about 30% petrochemical emollient and between about 20% to about 30% natural emollient.

3. The composition of claim 1 wherein the metal or metalloid oxide, hydroxide or carbonate is selected from the group consisting of aluminium, zinc, lead, iron, barium, tin, titanium, silicon, beryllium, magnesium and calcium.

4. The composition of claim 1 wherein the metal or metalloid oxide, hydroxide or carbonate is selected from the group consisting of aluminium oxide, tin oxide, zinc oxide, lead oxide, beryllium oxide, iron oxide, magnesium oxide, calcium oxide, titanium dioxide, silicon dioxide, aluminium hydroxide, zinc hydroxide, magnesium carbonate, calcium carbonate, aluminium carbonate, zinc carbonate, iron carbonate, and barium carbonate.

5. The composition of claim 4 wherein the metal or metalloid oxide, hydroxide or carbonate is selected from the group consisting of zinc oxide, zinc carbonate, titanium dioxide, and iron (III) oxide.

6. The composition of claim 1 wherein the metal or metalloid oxide, hydroxide or carbonate in the composition comprises between about 5% to about 20% calamine and between about 5% to about 20% of a further metal or metalloid oxide, hydroxide or carbonate.

7. The composition of claim 6 wherein the further metal or metalloid oxide, hydroxide or carbonate comprises zinc oxide.

8. The composition of claim 1, further comprising at least one preservative.

9. The composition of claim 8 wherein the at least one preservative is selected from *Eucalyptus* oil and a piroctone salt or derivative.

10. The composition of claim 9 wherein the *Eucalyptus* oil is present, in % by weight of the composition, from about 1.0% to about 6%.

11. The composition of claim 1 comprising, in % by weight amounts of the composition, about 10% to about 15% jojoba oil, about 5% to about 10% emu oil, about 2% to about 5% *Eucalyptus* oil, about 10% to about 15% zinc oxide, about 10% to about 15% calamine, about 15% to about 35% of a petrochemical emollient selected from petroleum jelly and paraffin and about 15% to about 35% of a natural emollient selected from shea butter, beeswax, lanolin and a lanolin-based emollient.

12. A method of treating and/or preventing a skin condition in a subject, the method including the step of administering to the skin of the subject a therapeutically effective amount of an emollient composition comprising, in % by weight amounts of the composition:

(a) about 2.5% to about 15% emu oil;
(b) about 4% to about 25% jojoba oil;
(c) about 25% to about 75% of a dermatological base wherein the dermatological base comprises at least two emollients wherein one is a petrochemical emollient and one is a natural emollient and wherein the petrochemical emollient is selected from petroleum jelly and paraffin and the natural emollient is selected from shea butter, beeswax, lanolin and a lanolin-based emollient; and
(d) about 10% to about 40% of a metal or metalloid oxide, hydroxide or carbonate.

13. The method of claim 12 wherein the skin condition is selected from the group consisting of dry skin, nappy rash, inflammation, erythema, psoriasis rashes, bed sores, allergic rashes, acne, rosacea, minor skin infections, and skin irritation rashes.

14. A method of formulating an emollient composition including the step of combining and mixing emu oil, jojoba oil, a dermatological base and a metal or metalloid oxide, hydroxide or carbonate to form the emollient composition in the following % by weight amounts of the composition:

(a) about 2.5% to about 15% emu oil;
(b) about 4% to about 25% jojoba oil;
(c) about 25% to about 75% dermatological base wherein the dermatological base comprises at least two emollients wherein one is a petrochemical emollient and one is a natural emollient and wherein the petrochemical emollient is selected from petroleum jelly and paraffin and the natural emollient is selected from shea butter, beeswax, lanolin and a lanolin-based emollient; and
(d) about 10% to about 40% metal or metalloid oxide, hydroxide or carbonate.

15. The method of claim 14 wherein the combining and mixing are carried out at below 40° C.

16. The composition of claim 1 wherein the natural emollient is lanolin or a lanolin-based emollient.

17. The composition of claim 1 wherein the paraffin is white soft paraffin.

18. An emollient composition comprising in % by weight amounts of the composition:

(a) about 2.5% to about 15% emu oil;
(b) about 4% to about 25% jojoba oil;
(c) about 25% to about 75% of a dermatological base wherein the dermatological base comprises at least two emollients wherein one is a petrochemical emollient selected from petroleum jelly and paraffin and one is a natural emollient selected from lanolin and a lanolin-based emollient; and
(d) about 10% to about 40% of a metal or metalloid oxide, hydroxide or carbonate.

* * * * *